United States Patent [19]
Chang et al.

[11] Patent Number: 5,859,225
[45] Date of Patent: Jan. 12, 1999

[54] VIRION PROTEIN 26 FROM KAPOSI'S SARCOMA-ASSOCIATED HERPESVIRUS, DNA ENCODING SAME AND USES THEREOF

[75] Inventors: Yuan Chang, New York, N.Y.; Roy A. Bohenzky, Mountain View, Calif.; James J. Russo, New York, N.Y.; Isidore S. Edelman, New York, N.Y.; Patrick S. Moore, New York, N.Y.

[73] Assignee: The Trustees of Columbia University in the City of New York, New York, N.Y.

[21] Appl. No.: 708,678

[22] Filed: Sep. 5, 1996

[51] Int. Cl.$^6$ .................. C07H 21/04; A61K 39/245; C12Q 1/68; C12N 7/00
[52] U.S. Cl. .................. 536/23.72; 424/229.1; 435/6; 435/235.1; 435/320.1
[58] Field of Search .................. 536/23.72; 424/229.1; 435/6, 235.1, 320.1

[56] References Cited

PUBLICATIONS

Ades et al. (1989) Prevalence of antibodies to herpes simplex virus types 1 and 2 in pregnant women, and estimated rates of infection, J Epidemiol Commun Health 43, 53–60 (Exhibit 2).

Booy et al. (1994) Finding a needle in a haystack: detection of a small protein (the 12–kDa VP26) in a large complex (the 200–MDa capsid of herpes simplex virus), Proc Natl Acad Sci USA 91, 5652–5656 (Exhibit 3).

Corey and Spear (1986) Infection with herpes simplex viruses, N Eng J Med 314, 686–691 (Exhibit 4).

Crawford (1994) Epstein–Barr virus, In: Zuckerman et al., eds., Principles And Practice of Clinical Virology, 3d edn., New York, Wiley, pp. 109–134 (Exhibit 5).

Hornef (1995) Coincidence of Epstein–Barr virus reactivation, cyto–megalovirus infection, and rejection episodes in renal transplant recipients, Transplantation 60, 474–480 (Exhibit 6).

Tatman et al. (1994) Assembly of herpes simplex virus type 1 capsids using a panel of recombinant baculoviruses, J Gen Virol 75, 1101–1113 (Exhibit 7).

Trus et al. (1995) Herpes simplex virus capsids assembled in insect cells infected with recombinant baculoviruses; structural authenticity and localization of VP26, J Virol 69, 7362–7366 (Exhibit 8).

van Grunsven etl (1993) Gene mapping and expression of two immuno–dominant Epstein–Barr virus capsid proteins, J Virol 67, 3908–3916 (Exhibit 9).

*Primary Examiner*—Ponnathapura Achutamurthy
*Assistant Examiner*—Phuong T. Bui
*Attorney, Agent, or Firm*—John P. White

[57] ABSTRACT

This invention provides an isolated nucleic acid molecule which encodes KSHV virion protein 26. This invention provides an isolated polypeptide molecule which encodes KSHV virion protein 26. This invention provides an antibody specific to the polypeptide. Antisense and triplex oligonucleotide molecules are also provided. This invention provides a vaccine and method of vaccination, prophylaxis, diagnosis and treatment of a subject with KS and detecting expression of a DNA virus associated with Kaposi's sarcoma in a cell.

14 Claims, 2 Drawing Sheets

FIGURE 1  KSHV LONG UNIQUE CODING REGION

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
      ( A ) LENGTH: 513 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:

( A ) NAME/KEY: CDS
( B ) LOCATION: 1..513

( x i ) SEQUENCE DESCRIPTION: SEQ ID NO:1:

| ATG | TCC | AAC | TTT | AAG | GTG | AGA | GAC | CCC | GTG | ATC | CAG | GAG | CGA | CTG | GAT | 48 |
|---|---|---|---|---|---|---|---|---|---|---|---|---|---|---|---|---|
| Met | Ser | Asn | Phe | Lys | Val | Arg | Asp | Pro | Val | Ile | Gln | Glu | Arg | Leu | Asp | |
| 1 | | | | 5 | | | | | 10 | | | | | 15 | | |

| CAT | GAC | TAC | GCT | CAC | CAT | CCC | CTG | GTG | GCT | CGC | ATG | AAT | ACC | CTG | GAT | 96 |
|---|---|---|---|---|---|---|---|---|---|---|---|---|---|---|---|---|
| His | Asp | Tyr | Ala | His | His | Pro | Leu | Val | Ala | Arg | Met | Asn | Thr | Leu | Asp | |
| | | | 20 | | | | | 25 | | | | | 30 | | | |

| CAG | GGA | AAT | ATG | TCG | CAG | GCC | GAA | TAC | CTC | GTG | CAA | AAG | AGA | CAC | TAT | 144 |
|---|---|---|---|---|---|---|---|---|---|---|---|---|---|---|---|---|
| Gln | Gly | Asn | Met | Ser | Gln | Ala | Glu | Tyr | Leu | Val | Gln | Lys | Arg | His | Tyr | |
| | | 35 | | | | | 40 | | | | | 45 | | | | |

| CTC | GTG | TTC | TTA | ATT | GCC | CAT | CAT | TAT | TAT | GAG | GCC | TAT | CTG | AGG | AGG | 192 |
|---|---|---|---|---|---|---|---|---|---|---|---|---|---|---|---|---|
| Leu | Val | Phe | Leu | Ile | Ala | His | His | Tyr | Tyr | Glu | Ala | Tyr | Leu | Arg | Arg | |
| | 50 | | | | | 55 | | | | | 60 | | | | | |

| ATG | GGT | GGA | ATT | CAA | AGG | CGG | GAT | CAT | CTG | CAG | ACC | CTT | AGG | GAT | CAG | 240 |
|---|---|---|---|---|---|---|---|---|---|---|---|---|---|---|---|---|
| Met | Gly | Gly | Ile | Gln | Arg | Arg | Asp | His | Leu | Gln | Thr | Leu | Arg | Asp | Gln | |
| 65 | | | | | 70 | | | | | 75 | | | | | 80 | |

| AAA | CCG | CGC | GAG | CGC | GCT | GAC | CGA | GTT | TCC | GCG | GCG | TCG | GCT | TAC | GAC | 288 |
|---|---|---|---|---|---|---|---|---|---|---|---|---|---|---|---|---|
| Lys | Pro | Arg | Glu | Arg | Ala | Asp | Arg | Val | Ser | Ala | Ala | Ser | Ala | Tyr | Asp | |
| | | | | 85 | | | | | 90 | | | | | 95 | | |

| GCG | GGG | ACG | TTC | ACC | GTG | CCT | TCG | AGG | CCA | GGC | CCT | GCA | TCC | GGC | ACC | 336 |
|---|---|---|---|---|---|---|---|---|---|---|---|---|---|---|---|---|
| Ala | Gly | Thr | Phe | Thr | Val | Pro | Ser | Arg | Pro | Gly | Pro | Ala | Ser | Gly | Thr | |
| | | | 100 | | | | | 105 | | | | | 110 | | | |

| ACG | CCC | GGG | GGC | CAG | GAC | TCA | CTG | GGG | GTC | TCG | GGA | AGC | AGT | ATA | ACC | 384 |
|---|---|---|---|---|---|---|---|---|---|---|---|---|---|---|---|---|
| Thr | Pro | Gly | Gly | Gln | Asp | Ser | Leu | Gly | Val | Ser | Gly | Ser | Ser | Ile | Thr | |
| | | 115 | | | | | 120 | | | | | 125 | | | | |

| ACC | CTG | TCC | TCT | GGT | CCC | CAT | TCA | TTG | TCG | CCG | GCG | TCA | GAC | ATT | CTC | 432 |
|---|---|---|---|---|---|---|---|---|---|---|---|---|---|---|---|---|
| Thr | Leu | Ser | Ser | Gly | Pro | His | Ser | Leu | Ser | Pro | Ala | Ser | Asp | Ile | Leu | |
| | 130 | | | | | 135 | | | | | 140 | | | | | |

| ACA | ACC | CTC | TCA | TCC | ACG | ACG | GAA | ACG | GCC | GCC | CCC | GCG | GTG | GCC | GAC | 480 |
|---|---|---|---|---|---|---|---|---|---|---|---|---|---|---|---|---|
| Thr | Thr | Leu | Ser | Ser | Thr | Thr | Glu | Thr | Ala | Ala | Pro | Ala | Val | Ala | Asp | |
| 145 | | | | | 150 | | | | | 155 | | | | | 160 | |

| GCG | AGG | AAA | CCC | CCC | TCT | GGC | AAA | AAG | AAA | TAG | | | | | | 513 |
|---|---|---|---|---|---|---|---|---|---|---|---|---|---|---|---|---|
| Ala | Arg | Lys | Pro | Pro | Ser | Gly | Lys | Lys | Lys | * | | | | | | |
| | | | | 165 | | | | | 170 | | | | | | | |

( 2 ) INFORMATION FOR SEQ ID NO:2:

( i ) SEQUENCE CHARACTERISTICS:
( A ) LENGTH: 170 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Ser | Asn | Phe | Lys | Val | Arg | Asp | Pro | Val | Ile | Gln | Glu | Arg | Leu | Asp |
|---|---|---|---|---|---|---|---|---|---|---|---|---|---|---|---|
| 1 | | | | 5 | | | | | 10 | | | | | 15 | |

| His | Asp | Tyr | Ala | His | His | Pro | Leu | Val | Ala | Arg | Met | Asn | Thr | Leu | Asp |
|---|---|---|---|---|---|---|---|---|---|---|---|---|---|---|---|
| | | | 20 | | | | | 25 | | | | | 30 | | |

| Gln | Gly | Asn | Met | Ser | Gln | Ala | Glu | Tyr | Leu | Val | Gln | Lys | Arg | His | Tyr |
|---|---|---|---|---|---|---|---|---|---|---|---|---|---|---|---|
| | | 35 | | | | | 40 | | | | | 45 | | | |

| Leu | Val | Phe | Leu | Ile | Ala | His | His | Tyr | Tyr | Glu | Ala | Tyr | Leu | Arg | Arg |
|---|---|---|---|---|---|---|---|---|---|---|---|---|---|---|---|
| | 50 | | | | | 55 | | | | | 60 | | | | |

| Met | Gly | Gly | Ile | Gln | Arg | Arg | Asp | His | Leu | Gln | Thr | Leu | Arg | Asp | Gln |
|---|---|---|---|---|---|---|---|---|---|---|---|---|---|---|---|
| 65 | | | | | 70 | | | | | 75 | | | | | 80 |

| Lys | Pro | Arg | Glu | Arg | Ala | Asp | Arg | Val | Ser | Ala | Ala | Ser | Ala | Tyr | Asp |
|---|---|---|---|---|---|---|---|---|---|---|---|---|---|---|---|
| | | | | 85 | | | | | 90 | | | | | 95 | |

| Ala | Gly | Thr | Phe | Thr | Val | Pro | Ser | Arg | Pro | Gly | Pro | Ala | Ser | Gly | Thr |
|---|---|---|---|---|---|---|---|---|---|---|---|---|---|---|---|

|  | | | | | 100 | | | | 105 | | | | 110 | |
|---|---|---|---|---|---|---|---|---|---|---|---|---|---|---|
| Thr | Pro | Gly<br>115 | Gly | Gln | Asp | Ser | Leu<br>120 | Gly | Val | Ser | Gly | Ser<br>125 | Ser | Ile | Thr |
| Thr | Leu<br>130 | Ser | Ser | Gly | Pro | His<br>135 | Ser | Leu | Ser | Pro | Ala<br>140 | Ser | Asp | Ile | Leu |
| Thr<br>145 | Thr | Leu | Ser | Ser | Thr<br>150 | Thr | Glu | Thr | Ala | Ala<br>155 | Pro | Ala | Val | Ala | Asp<br>160 |
| Ala | Arg | Lys | Pro | Pro<br>165 | Ser | Gly | Lys | Lys | Lys<br>170 | | | | | | |

( 2 ) INFORMATION FOR SEQ ID NO:3:

( i ) SEQUENCE CHARACTERISTICS:
    ( A ) LENGTH: 330 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:3:

| GGATCCCTCT | GACAACCTTC | AGATAAAAAA | CGTATATGCC | CCCTTTTTTC | AGTGGGACAG | 60 |
|---|---|---|---|---|---|---|
| CAACACCCAG | CTAGCAGTGC | TACCCCCATT | TTTTAGCCGA | AAGGATTCCA | CCATTGTGCT | 120 |
| CGAATCCAAC | GGATTTGACC | CCGTGTTCCC | CATGGTCGTG | CCGCAGCAAC | TGGGGCACGC | 180 |
| TATTCTGCAG | CAGCTGTTGG | TGTACCACAT | CTACTCCAAA | ATATCGGCCG | GGCCCCGGA  | 240 |
| TGATGTAAAT | ATGGCGGAAC | TTGATCTATA | TACCACCAAT | GTGTCATTTA | TGGGGCGCAC | 300 |
| ATATCGTCTG | GACGTAGACA | ACACGGATCC | | | | 330 |

( 2 ) INFORMATION FOR SEQ ID NO:4:

( i ) SEQUENCE CHARACTERISTICS:
    ( A ) LENGTH: 627 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:4:

| GGATCCGCTG | GCAGGTGGGC | GCGCACCTCG | TCGGGTAGCT | TGGAGACAAA | CAGCTCCAGG | 60 |
|---|---|---|---|---|---|---|
| CCAGTCCGCG | CCGTAGCGCC | TGCAGGTGCC | TCACCACCGG | GGCCGGGTCA | TGCGATCTGT | 120 |
| TTAGTCCGGA | GAAGATAGGG | CCCTTGGGAA | GCCGCTGAAC | CAGCTCCAGG | GTCTCCAAGA | 180 |
| TGCGCACCGG | TTGTCGGAGC | TGTCGCGATA | GAGGTTAGGG | TAGGTGTCCG | GTCCGTCCGT | 240 |
| GGGCTCAAAC | CTGCCCAGAC | ACACCACTGT | CTGCTGGGGG | ATCATCCTTC | TCAGGGAGAT | 300 |
| GCATTCTTTG | GAAGTAGTGG | TAGAGATGGA | GCAGACTGCC | AGGGCGTTGC | AGGAGTGGTG | 360 |
| GCGATGGTGC | GCACCGTTTT | TAAGAAACCC | CCAGGGTGG  | GGACTCCCGC | TCCCTGCAGC | 420 |
| ATCTCGGCCT | GCTGTACGTC | CTTGGCGAAT | ATGCGACGAA | ATCGGCTGTG | CGCACGGGT  | 480 |
| CCCAGGGCCG | GTCCGGTGGC | ATACAGGCCG | GTGAGGGCCC | CCTGGGTCTG | TCCGCCTGGA | 540 |
| AACAGGGTGC | TGTGAAACAA | CAGGTTGCAA | GGCCGCGAAT | ACCCCTCTGC | ACGCTGCTGT | 600 |

GGACGTGGGT GTATGCTCCG TGGATCC 627

( 2 ) INFORMATION FOR SEQ ID NO:5:

( i ) SEQUENCE CHARACTERISTICS:
        ( A ) LENGTH: 199 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:5:

CTAACAACGC GGCCCTTGCC ATTCGAGACC TAGATCAAAC TGTCAGTTTT GTAGTGCCTT 60

GCCTTGGGAC GCCCGACTGC GAGGCTGCCC TATTAAAGCA CCGTGACGTG CGCGGACTGC 120

TTCAGCTCAC CTCACAGCTG CTGGAGTTCT GTTGCGGGAA GTGTTCCTCC TGAGGCTATT 180

TCGCCCGCCT GTGTGGAAG 199

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:6:

AGCCGAAAGG ATTCCACCAT 20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:7:

TCCGTGTTGT CTACGTCCAG 20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:8:

GAAATTACCC ACGAGATCGC                                                                              20

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:9:

AGGCAACGTC AGATGTGA                                                                                18

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:10:

AACACGTCAT GTGCAGGAGT GAC                                                                          23

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:11:

CGGGTGACAG TTGTGATCTA AGG                                                                          23

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:12:

AGCCATCGCA GGGCAGTACG                                                                              20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:13:

GACTCTTCGC TGATGAACTG G        21

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:14:

AGGCAACGTC AGATGTGAC        19

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:15:

CATGGGAGTA CATTGTCAGG ACCTC        25

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:16:

GGAATTATCT CGCAGGTTGC C        21

( 2 ) INFORMATION FOR SEQ ID NO:17:

( i ) SEQUENCE CHARACTERISTICS:

(A) LENGTH: 23 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:17:

GGCGACATTC ATCAACCTCA GGG                                                                                  23

(2) INFORMATION FOR SEQ ID NO:18:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:18:

ATATCATCCT GTGCGTTCAC GAC                                                                                  23

(2) INFORMATION FOR SEQ ID NO:19:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:19:

CATGGGAGTA CATTGTCAGG ACCTC                                                                                25

VIRION PROTEIN 26 FROM KAPOSI'S SARCOMA-ASSOCIATED HERPESVIRUS, DNA ENCODING SAME AND USES THEREOF

The invention disclosed herein was made with Government support under a co-operative agreement CCU210852 from the Centers for Disease Control and Prevention, of the Department of Health and Human Services and under National Institutes of Health, National Cancer Institute award CA67391. Accordingly, the U.S. Government has certain rights in this invention.

Throughout this application, various publications may be referenced by Arabic numerals in brackets. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Kaposi's sarcoma-associated herpesvirus (KSHV) is a new human herpesvirus (HHV8) believed to cause Kaposi's sarcoma (KS) [1,2].

Kaposi's sarcoma is the most common neoplasm occurring in persons with acquired immunodeficiency syndrome (AIDS). Approximately 15–20% of AIDS patients develop this neoplasm which rarely occurs in immunocompetent individuals. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS. KS is uncommon among adult AIDS patients infected through heterosexual or parenteral HIV transmission, or among pediatric AIDS patients infected through vertical HIV transmission. Agents previously suspected of causing KS include cytomegalovirus, hepatitis B virus, human papillomavirus, Epstein-Barr virus (EBV), human herpesvirus 6, human immunodeficiency virus (HIV), and Mycoplasma penetrans. Non-infectious environmental agents, such as nitrite inhalants, also have been proposed to play a role in KS tumorigenesis. Extensive investigations, however, have not demonstrated an etiologic association between any of these agents and AIDS-KS.

Virion protein 26 (VP26) is a component of the nucleocapsid structure in most herpesviruses. This structure serves as a delivery mechanism for the viral genome as it is spread from one infected cell to another. As part of the original infecting virus, it is recognized as a major antigen by the immune system and can therefore be used to screen for antibodies to the herpesvirus in patient sera and as a vaccine.

SUMMARY OF THE INVENTION

This invention provides an isolated nucleic acid molecule which encodes KSHV virion protein 26. This invention provides an isolated polypeptide molecule which encodes KSHV virion protein 26.

This invention provides an antibody specific to the polypeptide. Antisense and triplex oligonucleotide molecules are also provided.

This invention provides a vaccine and method of vaccination, prophylaxis, diagnosis and treatment of a subject with KS and detecting expression of a DNA virus associated with Kaposi's sarcoma in a cell.

DETAILED DESCRIPTION OF THE INVENTION

Definitions

Figure 1:
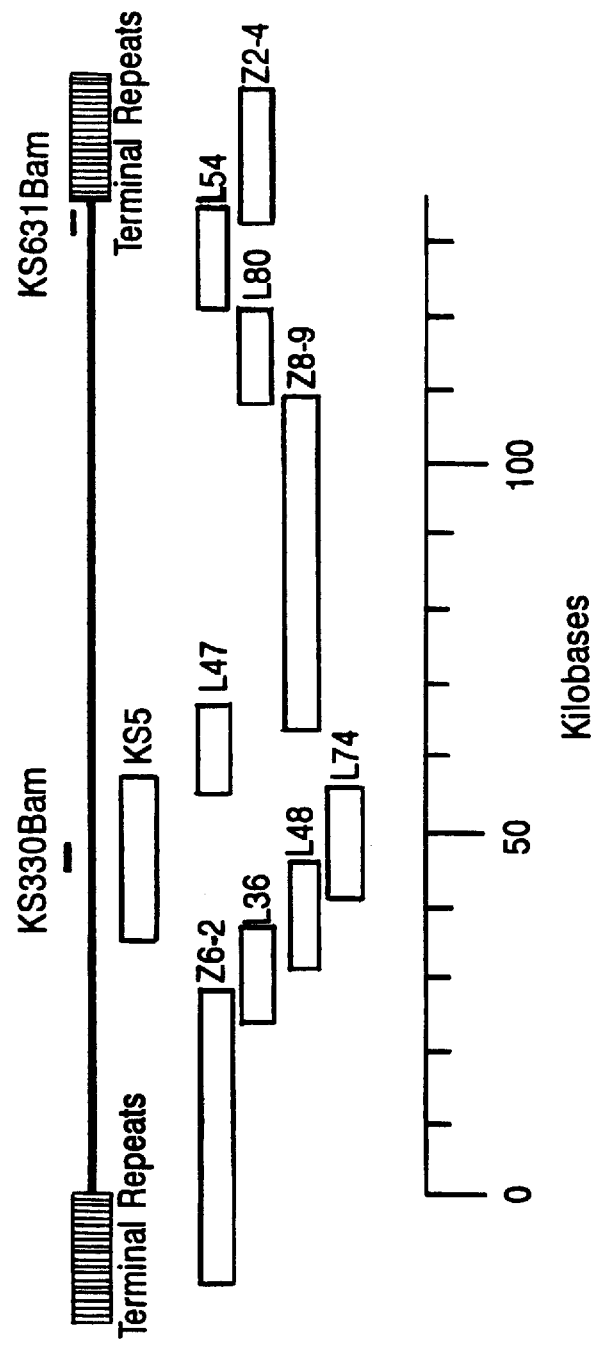
FIG. 1 Map of the KSHV/HHV8 genome. Overlapping cosmid (Z-#) and lambda phage (L-#) clone inserts are also shown.
Figure 2:
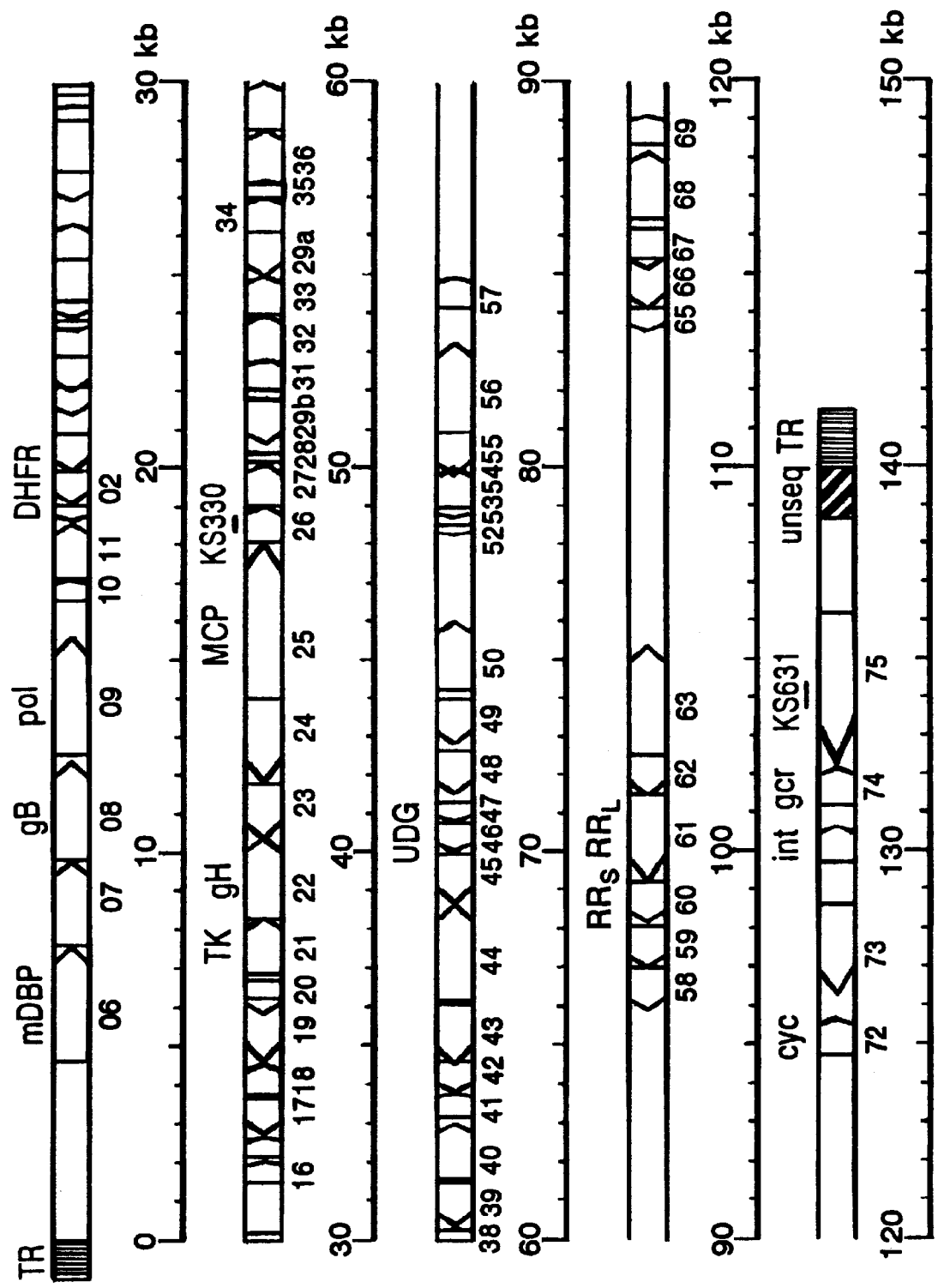
FIG. 2 Gene map of the KSHV sequence based on sequencing of the cosmid and lambda inserts shown in FIG. 1. Numbers indicate open reading frames (ORFs) corresponding to related genes in herpesvirus saimiri (HVS). Terminal repeat (TR). Proteins identified by sequence relatedness include, but are not limited to: single-stranded DNA binding protein (mDBP/SSBP), glycoprotein B (gB), DNA-dependent DNA polymerase (pol), dihydrofolate reductase (DHFR), thymidine kinase (TK), glycoprotein H (gH), major capsid protein (MCP), uracil-DNA glycosylase (UDG), ribonucleotide reductase small subunit ($RR_S$), ribonucleotide reductase large subunit ($RR_L$), cyclin D (cyc) integrin (int), G-protein coupled receptor (gcr)

The following standard abbreviations are used throughout the specification to indicate specific nucleotides:

| | |
|---|---|
| C = cytosine | A = adenosine |
| T = thymidine | G = guanosine |

The term "nucleic acid", as used herein, refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double- stranded polymer of deoxyribonucleotide or ribonucleotide bases read from the 5' to the 3' end. It includes both self-replicating plasmids, infectious polymers of DNA or RNA and nonfunctional DNA or RNA.

The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. 0.2×SSC refers to a solution 0.2 times the SSC concentration or 0.03M sodium chloride and 4 mM sodium citrate.

The phrase "selectively hybridizing to" and the phrase "specific hybridization" describe a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization.

"Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al.(1989) *Molecular Cloning: A Laboratory Manual* (2nd ed.), Cold Spring Harbor Laboratory, Vols. 1–3 or Ausubel, F., et al. (1987) *Current Protocols in Molecular Biology*, New York.

The phrase "nucleic acid molecule encoding" refers to a nucleic acid molecule which directs the expression of a specific polypeptide. The nucleic acid sequences include both the DNA strand sequence that is transcribed into RNA, the complementary DNA strand, and the RNA sequence that is translated into protein. The nucleic acid molecule includes both the full length nucleic acid sequence as well as non-full length sequences. It being further understood that the sequence includes the degenerate codons of the native sequence or sequences which may be introduced to provide codon preference in a specific host cell.

A nucleic acid probe is "specific" for a target organism of interest if it includes a nucleotide sequence which when detected is determinative of the presence of the organism in the presence of a heterogeneous population of proteins and other biologics. A specific nucleic acid probe is targeted to that portion of the sequence which is determinative of the organism and will not hybridize to other sequences, especially those of the host, where a pathogen is being detected.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types.

Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a polypeptide produced using non-native cells. The cells produce the protein because they have been genetically altered by the introduction of the appropriate nucleic acid sequence.

The following terms are used to describe the sequence relationships between two or more nucleic acid molecules: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences in a comparison window may be conducted by the algorithm of Smith and Waterman (1981) *Adv. Appl. Math.* 2:482, by the algorithm of Needleman and Wunsch (1970) *J. Mol. Biol.* 48:443, by the search-for-similarity method of Pearson and Lipman (1988) *Proc. Natl. Acad. Sci.* 85:2444, or by computerized implementations of these algorithms (GAP, BESTFIT, FASTA, and TFASTA in GCG, the Wisconsin Genetics Software Package Release 8.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties, such as charge or polarity, are not likely to effect the properties of a protein. Examples include glutamine for asparagine or glutamic acid for aspartic acid.

The phrase "substantially purified" or "isolated" when referring to a herpesvirus polypeptide, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a polypeptide, refers to a binding reaction which is determinative of the presence of the KSHV polypeptide of the invention in the presence of a heterogeneous population of polypeptides and other biologics including viruses other than KSHV. Thus, under designated immunoassay conditions, the specified antibodies bind to the KSHV antigen and do not bind in a significant amount to other antigens present in the sample.

"Specific binding" to an antibody under such conditions may require an antibody that is selected for its specificity for a particular antigen. For example, antibodies raised to KSHV antigens described herein can be selected to obtain antibodies specifically immunoreactive with KSHV polypeptides and not with other polypeptides.

"Biological sample" as used herein refers to any sample obtained from a living organism or from an organism that has died. Examples of biological samples include body fluids and tissue specimens.

It will be readily understood by those skilled in the art and it is intended here, that when reference is made to particular sequence listings, such reference includes sequences which substantially correspond to the listing and it's complement, including allowances for minor sequencing errors, single base changes, deletions, substitutions and the like, such that any such sequence variation corresponds to the nucleic acid sequence of the pathogenic organism or disease marker to which the relevant sequence listing relates.

I. Virion Protein 26 (VP26) from KSHV

This invention provides an isolated nucleic acid molecule which encodes Kaposi's sarcoma-associated herpesvirus (KSHV) virion protein 26 (VP26).

In one embodiment, the isolated nucleic acid molecule which encodes VP26 has the nucleotide sequence as set forth in SEQ ID NO:1. In another embodiment, the isolated nucleic acid molecule which encodes VP26 has the amino acid sequence as set forth in SEQ ID NO:2.

In one embodiment, the isolated nucleic acid molecule has the 5' untranslated sequence as set forth in SEQ ID NO:5. In another embodiment, the isolated nucleic acid molecule which encodes VP26 has the nucleotide sequence as set forth in SEQ ID NO:5 and SEQ ID NO:1.

In one embidiment the isolated nucleic acid molecule is genomic DNA. In another embodiment the isolated nucleic acid molecule is cDNA. In another embodiment RNA is derived from the isolated nucleic acid molecule or is capable of hybridizing with the isolated nucleic acid molecule.

Further, the nucleic acid molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post- transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

Virion protein 26 from KSHV is a component of the KSHV nucleocapsid structure. VP26 from KSHV is recognized as a major antigen by the immune system and can therefore be used to screen for antibodies to KSHV in patient sera and as a vaccine against KSHV infection.

A. Isolation and Propagation of KSHV

KSHV can be propagated in vitro. For example, techniques for growing herpesviruses have been described by Ablashi, D. V., et al. in *Virology* 184:545–552. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 µg/ml polybrene for 2 hours at 37° C. prior to infection. Infected cells are observed by demonstrating morphological changes, as well as being viral antigen positive.

For KSHV isolation, the virus is either harvested directly from cell culture fluid by centrifugation, or the infected cells are harvested, homogenized or lysed and the virus is separated from cellular debris and purified by standard methods of isopycnic sucrose density gradient centrifugation.

One skilled in the art may isolate and propagate KSHV employing the following protocol. Long- term establishment of a B lymphoid cell line infected with KSHV (e.g., RCC-1, HBL-6 or BCBL-1) is accomplished using body-cavity based lymphomas and standard techniques (Glick, J. L. (1980) *Fundamentals of Human Lymphoid Culture*, Marcel Dekker, New York; Knowles, D. M., et al. (1989) *Blood* 73:792–798; Metcalf, D. (1984) *Clonal Culture of Hematopoeitic Cells: Techniques and Applications*, Elvier, N.Y.).

Fresh lymphoma tissue containing viable infected cells is filtered to form a single cell suspension. The cells are separated by Ficoll-Plaque centrifugation and lymphocyte layer is removed. The lymphocytes are then placed at $>1\times10^6$ cells/ml into standard lymphocyte tissue culture medium, such as RPMI 1640 supplemented with 10% fetal calf serum. Immortalized lymphocytes containing KSHV are indefinitely grown in the culture media while nonimmortalized cells die during course of prolonged cultivation.

Further, KSHV may be propagated in a new cell line by removing media supernatant containing the virus from a continuously-infected cell line at a concentration of $>1\times10^6$ cells/ml. The media is centrifuged at 2000×g for 10 minutes and filtered through a 0.45µ filter to remove cells. The media is applied in a 1:1 volume with cells growing at $>1\times10^6$ cells/ml for 48 hours. The cells are washed, pelleted and placed in fresh culture medium, then tested for KSHV after 14 days. KSHV may be isolated from a cell line in the following manner. An infected cell line is lysed using standard methods, such as hyposomatic shock or Dounce homogenization or using repeated cycles of freezing and thawing in a small volume (<3 ml), and pelleted at 2000×g for 10 minutes. The supernatant is removed and centrifuged again at 10,000×g for 15 minutes to remove nuclei and organelles. The resulting low-speed, cell-free supernatant is filtered through a 0.45µ filter and centrifuged at 100,000×g for 1 hour to pellet the virus. The virus can then be washed and re-pelleted. The DNA is extracted from the viral pellet by standard techniques (e.g., phenol/chloroform) and tested for the presence of KSHV by Southern blotting and/or PCR using the specific probes described above.

For banding whole virion, the low-speed cell-free supernatant is adjusted to contain 7% PEG-8000. The PEG-supernatant is spun at 10,000×g for 30 min. The supernatant is poured off and :he pellet collected and resuspended in a small volume (1–2 ml) of virus buffer (VB, 0.1M NaCl, 0.01M Tris, pH 7.5). The virion are isolated by centrifugation at 25,000 rpm in a 10–50% sucrose gradient made with VB. One ml fractions of the gradient are obtained by standard techniques (e.g., using a fractionator) and each fraction is tested by dot blotting using specific hybridizing probes to determine the gradient fraction containing the purified virus (preparation of the fraction is needed in order to detect the presence of the virus, i.e., standard DNA extraction).

The method for isolating the KSHV genome is based on Pellicer et alia (1978) *Cell* 14:133–141 and Gibson and Roizmann (1972) *J. Virol.* 10:1044–52.

A final method for isolating the KSHV genome is clamped homogeneous electric field (CHEF) gel electrophoresis. Agarose plugs are prepared by resuspending cells infected with KSHV in 1% LMP agarose (Biorad) and 0.9% NaCl at 42° C. to a final concentration of $2.5\times10^7$ cells/ml. Solidified agarose plugs are transferred into lysis buffer (0.5M EDTA pH 8.0, 1% sarcosyl, proteinase K at 1 mg/ml final concentration) and incubated for 24 hours. Approximately $10^7$ cells are loaded in each lane. Gels are run at a gradient of 6.0 V/cm with a run time of 28 h on a CHEF Mapper XA pulsed field gel electrophoresis apparatus (Biorad), Southern blotted and hybridized to KS627Bam, KS330Bam and an EBV terminal repeat sequence.

To make a new cell line infected with KSHV, already-infected cells are co-cultivated with a Raji cell line separated by a 0.45µ filter. Approximately, $1-2\times10^6$ already-infected BCBL-1 and $2\times10^6$ Raji cells are co-cultivated for 2–20 days in supplemented RPMI alone or with 20 ng/ml 12-O-tetradecanoyl phorbol-13-acetate (TPA). After 2–20 days co-cultivation, Raji cells are removed, washed and placed in supplemented RPMI 1640 media. A Raji culture co-cultivated with BCBL-1 in 20 ng/ml TPA for 2 days survived and has been kept in continuous suspension culture for >10 weeks. This cell line, designated RCC-1 (Raji Co-Culture, No.1) remains PCR positive for the KSHV sequence after multiple passages. RCC-1 cells periodically undergo rapid cytolysis suggestive of lytic reproduction of KSHV. Thus, RCC-1 is a Raji cell line newly-infected with KSHV.

RCC-1 and RCC-$1_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. HBL-6 was deposited (as BHL-6) on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

PCR amplification of the viral genome can be carried out, for example, using the following three sets of PCR primers:

1) AGCCGAAAGGATTCCACCAT (SEQ ID NO: 6),
   TCCGTGTTGTCTACGTCCAG (SEQ ID NO: 7);

2) GAAATTACCCACGAGATCGC (SEQ ID NO: 8),
   AGGCAACGTCAGATGTGA (SEQ ID NO: 9);

3) AACACGTCATGTGCAGGAGTGAC (SEQ ID NO:10),
   CGGGTGACAGTTGTGATCTAAGG (SEQ ID NO:11).

In PCR techniques, oligonucleotide primers, as listed above, complementary to the two 3' borders of the DNA region to be amplified are synthesized. The polymerase chain reaction is then carried out using the two primers. See *PCR Protocols: A Guide to Methods and Applications* (1990) Innis, M., Gelfand D., Sninsky, J. and White, T., Eds., Academic Press, San Diego. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Alternatively, PCR identification of KSHV can be performed with the following nested primer sets:

No.1 outer AGCACTCGCAGGGCAGTACG (SEQ ID NO: 12),
         GACTCTTCGCTGATGAACTGG (SEQ ID NO: 13);
No.1 inner TCCGTGTTGTCTACGTCCAG (SEQ ID NO: 7),
         AGCCGAAAGGATTCCACCAT (SEQ ID NO: 6);
No.2 outer AGGCAACGTCAGATGTGAC (SEQ ID NO: 14),
         GAAATTACCCACGAGATCGC (SEQ ID NO: 8);
No.2 inner CATGGGAGTACATTGTCAGGACCTC (SEQ ID NO: 15),
         GGAATTATCTCGCAGGTTGCC (SEQ ID NO: 16);
No.3 outer GGCGACATTCATCAACCTCAGGG (SEQ ID NO: 17),
         ATATCATCCTGTGCGTTCACGAC (SEQ ID NO: 18);
No.3 inner CATGGGAGTACATTGTCAGGACCTC (SEQ ID NO: 19),
         GGAATTATCTCGCAGGTTGCC (SEQ ID NO:16).

The outer primer set is amplified for 35 cycles at 94° C. for 30 seconds, 60° C. for 1 minute and 72° C. for 1 minute with a 5 minute final extension cycle at 72° C. One ul of the PCR product is added to the inner PCR reaction mixture and amplified for 25 additional cycles. Primary determination of sample positivity is made with primer set 1 and confirmed with either primer sets 2 or 3 which amplify nonoverlapping regions of the KSHV major capsid gene. Sampling two portions of the KSHV genome decreases the likelihood of intraexperimental PCR contamination. These nested primer sets are 2–3 logs more sensitive for detecting KSHV sequences than the previously published $KS330_{233}$ primers and are estimated to be able to detect <10 copies of KSHV genome under optimal conditions.

B. Immunologic Identity of KSHV

In order to produce antisera for use in an immunoassay, a polypeptide is isolated which is encoded by the amino acid sequence of SEQ ID NO:2.

For example, recombinant polypeptide can be produced in a mammalian cell line or in bacteria (*E. coli*). An inbred strain of mice such as balb/c is immunized with the polypeptide using a standard adjuvant, such as Freund's adjuvant, and a standard mouse immunization protocol (Harlow and Lane (1988) *Antibodies, A Laboratory Manual*, Cold Spring Harbor Publication, New York). Alternatively, a synthetic peptide derived from the sequence disclosed herein and conjugated to a carrier protein can be used an immunogen. Polyclonal sera are collected and titered against the immunogen polypeptide in an immunoassay, for example, a solid phase immunoassay with the immunogen immobilized on a solid support. Polyclonal antisera with a titer of $10^4$ or greater are selected and tested for their cross reactivity against other viral antigens of the gammaherpesvirinae subfamily, particularly human herpes virus types 1–7, by using a standard immunoassay as described in Harlow and Lane.

The ability of the above viruses to compete with the binding of the antisera to the immunogen polypeptide is determined. The percent crossreactivity for other viruses is calculated, using standard calculations. Those antisera with less than 10% cross-reactivity with each of the other viruses listed above is selected and pooled. The cross-reacting antibodies are then removed from the pooled antisera by immunoabsorption with the above-listed viruses.

The immunoabsorbed and pooled antisera are then used in a competitive binding immunoassay procedure to compare an unknown (test) viral antigen preparation to the specific KSHV antigen preparation described herein and containing the nucleotide sequence described in SEQ ID NO:1. In order to make this comparison, the immunogen polypeptide which is encoded by the amino acid sequence of SEQ ID NO:2 is the labeled antigen and the test viral antigen preparations are each assayed at a wide range of concentrations. The amount of each test preparation required to inhibit 50% of the binding of the antisera to the labeled immunogen polypeptide is determined. Those viral antigens that specifically bind to an antibody generated to an immunogen consisting of the polypeptide of SEQ ID NO:2 are those where the amount of antigen needed to inhibit 50% of the binding to the polypeptide does not exceed an established amount. This amount is no more than 10 times the amount of the antigen that is needed for 50% inhibition for KSHV containing the nucleotide sequence of SEQ ID NO:1. Thus, the KSHV polypeptide of the invention can be defined by immunological comparison to the specific strain of KSHV for which nucleotide sequences are provided herein.

C. Hybridization Probes of KSHV VP26

This invention provides a nucleic acid sequence of at least 14 nucleotides capable of specifically hybridizing with the isolated nucleic acid molecule of SEQ ID NO:1.

In one embodiment the sequence may be 8–25 nucleotides. In another embodiment the sequence may be 14–20 nucleotides. In a preferred embodiment the sequence may be 14 nucleotides. In another preferred embodiment the sequence is greater than 16 nucleotides.

In one embodiment the molecule is DNA. In another embodiment the molecule is RNA.

High stringency hybridization conditions are selected at about 5° C. lower than the thermal melting point ($T_m$) for the specific sequence at a defined ionic strength and pH. The $T_m$ is the temperature (under defined ionic strength and pH) at which 50% of the the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6× SSC solution, washing at room temperature with 6× SSC solution, followed by washing at about 68° C. in a 0.6× SSC solution.

Hybridization with moderate stringency may be attained for example by: 1) filter pre-hybridizing and hybridizing with a solution of 3× SSC, 50% formamide, 0.1M Tris buffer at Ph 7.5, 5× Denhardt's solution; 2) pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature in 4× SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, *Tetrahedron Lett.* 22:1859–1862, or by the triester method according to Matteucci, et al., 1981, *Am. Chem. Soc.* 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The nucleic acid molecules of the subject invention also include molecules coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

D. Polypeptides of KSHV VP26 and Antibodies (Ab's) Thereto

This invention provides an isolated polypeptide encoding KSHV VP26. In one embodiment, the isolated polypeptide has the amino acid sequence as set forth in SEQ ID NO:2. In another embodiment the isolated polypeptide is encoded by a nucleic acid molecule with a sequence as set forth in SEQ ID NO:1.

This invention provides an isolated KSHV VP26 polypeptide encoded by the isolated nucleic acid molecule of KSHV. This invention provides a host cell which expresses the polypeptide of the isolated nucleic acid molecule.

Further, the isolated polypeptide may be linked to a second polypeptide to form a fusion protein by linking the isolated nucleic acid molecule to a second nucleic acid molecule and expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated nucleic acid molecule. In one embodiment the antibody is a monoclonal antibody. In another embodiment the antibody is a polyclonal antibody. In another embodiment the antibody is an anti-idiotypic antibody.

An antibody, polypeptide or isolated nucleic acid molecule may be labelled with a detectable marker including, but not limited to: a radioactive label, or a colorimetric, a luminescent, or a fluorescent marker, or gold. Radioactive labels include, but are not limited to: $^{3}H$, $^{14}C$, $^{32}P$, $^{33}P$; $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include, but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody, polypeptide or nucleic acid molecule may be detected by a second antibody which may be linked to an enzyme, such as alkaline phosphatase or horseradish peroxidase. Other enzymes which may be employed are well known to one of ordinary skill in the art.

This invention provides a method of producing a polypeptide encoded by the isolated nucleic acid molecule, which comprises growing a host-vector system under suitable conditions permitting production of the polypeptide and recovering the polypeptide so produced. Suitable host cells include bacteria, yeast, filamentous fungal, plant, insect and mammalian cells. Host-vector systems for producing and recovering a polypeptide are well known to those skilled in the art and include, but are not limited to, *E. coli* and pMAL (New England Biolabs), the Sf9 insect cell-baculovirus expression system, and mammalian cells (such as HeLa, COS, NIH 3T3 and HEK293) transfected with a mammalian expression vector by Lipofectin (Gibco-BRL) or calcium phosphate precipitation or other methods to achieve vector entry into the cell. Those of skill in the art are knowledgeable in the numerous expression systems available for expression of KSHV polypeptide.

This invention provides a method to select specific regions on the polypeptide encoded by the isolated nucleic acid molecule of the DNA virus to generate antibodies. Amino acid sequences may be analyzed by methods well known to those skilled in the art to determine whether they produce hydrophobic or hydrophilic regions in the polypeptides which they build. In the case of cell membrane proteins, hydrophobic regions are well known to form the part of the polypeptide that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, nucleic acid may be cloned and expressed and the resulting polypeptide recovered and used as an immunogen.

Polyclonal antibodies against. the polypeptide may be produced by immunizing animals using a selected polypeptide. Monoclonal antibodies are prepared using hybridoma technology by fusing antibody producing B cells from immunized animals with myeloma cells and selecting the resulting hybridoma cell line producing the desired antibody, as described further below.

II. Immunoassays

The antibodies raised against KSHV antigens may be detectably labelled, utilizing conventional labelling techniques well-known to the art, as described above.

In addition, enzymes may be used as labels. Suitable enzymes include alkaline phosphatase, beta-galactosidase, glucose-6-phosphate dehydrogenase, maleate dehydrogenase and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; activity is thus measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

A description of a radioimmunoassay (RIA) may be found in: Laboratory Techniques in *Biochemistry and Molecular Biology* (1978) North Holland Publishing Company, New York, with particular reference to the chapter entitled "An Introduction to Radioimmune Assay and Related Techniques" by T. Chard. A description of general immunometric assays of various types can be found in the following U.S. Pat. Nos. 4,376,110 (David et al.) or 4,098,876 (Piasio).

A. Assays for KSHV VP26 Antigens

One can use immunoassays to detect the virus or its components. A general overview of the applicable technology is in Harlow and Lane (1988) *Antibodies, A Laboratory Manual*, Cold Spring Harbor Publication, New York.

In one embodiment, antibodies to KSHV antigens can be used. In brief, to produce antibodies, the polypeptide being targeted is expressed and purified. The product is injected into a mammal capable of producing antibodies. Either polyclonal or monoclonal antibodies (including recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane at pages 567–573 and 584–589.

Monoclonal antibodies or recombinant antibodies may be obtained by techniques familiar to those skilled in the art. Briefly, spleen cells or other lymphocytes from an animal immunized with a desired antigen are immortalized, commonly by fusion with a myeloma cell (see, Kohler and Milstein (1976) *Eur. J. Immunol.* 6:511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Newer techniques using recombinant phage antibody expression systems can also be used to generate monoclonal antibodies. See for example: McCafferty, J et al. (1990) *Nature* 348:552; Hoogenboom, H. R. et al . (1991) *Nuc. Acids Res*. 19:4133; and Marks, J. D. et al. (1991) *J. Mol Biol*. 222:581–597.

Methods for characterizing naturally processed peptides bound to MHC (major histocompatibility complex) I molecules have been developed. See, Falk et al., 1991, *Nature* 351:290 and PCT publication No. WO 92/21033 published Nov. 26, 1992. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey, et al., 1991, *Nature* 353:326), and of the human MHC class I molecule, HLA-A2.1 type by mass spectrometry (Hunt, et al., 1991, *Eur. J. Immunol*. 21:2963–2970). See also, Rötzschke and Falk, 1991, *Immunol. Today* 12:447, for a general review of the characterization of naturally processed peptides in MHC class I. Further, Marloes, et al., 1991, *Eur. J. Immunol*. 21:2963–2970, describe how class I binding motifs can be applied to the identification of potential viral immunogenic peptides in vitro.

The polypeptides described herein produced by recombinant technology may be purified by standard techniques well known to those of skill in the art. Recombinantly produced viral polypeptides can be directly expressed or expressed as a fusion protein. The protein is then purified by a combination of cell lysis (e.g., sonication) and affinity chromatography.

For fusion products, subsequent digestion of the fusion protein with an appropriate proteolytic enzyme releases the desired peptide.

The polypeptides may be purified to substantial purity by standard techniques well known in the art, including selective precipitation with such substances as ammonium sulfate, column chromatography, immunopurification methods, and others. See, for instance, Scopes, R., 1982, *Protein Purification: Principles and Practice*, Springer-Verlag, New York.

B. Assays for KSHV VP26 Antibodies

Antibodies reactive with antigens of KSHV can also be measured by a variety of immunoassay methods that are similar to the procedures described above for measurement of antigens. For a review of immunological and immunoassay procedures applicable to the measurement of antibodies by immunoassay techniques, see *Basic and Clinical Immunology* 7th Edition, D. Stites and A. Terr, Eds., and Harlow and Lane, 1988, *Antibodies, A Laboratory Manual*, Cold Spring Harbor Publication, New York.

In brief, immunoassays to measure antibodies reactive with antigens of KSHV can be either competitive or noncompetitive binding assays. In competitive binding assays, the sample analyte competes with a labeled analyte for specific binding sites on a capture agent bound to a solid surface. Preferably the capture agent is a purified recombinant human herpesvirus polypeptide produced as described above. Other sources of human herpesvirus polypeptides, including isolated or partially purified naturally occurring polypeptide, may also be used.

Noncompetitive assays are typically sandwich assays, in which the semple analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of the human herpesvirus antigens.

Hemagglutination Inhibition (HI) and Complement Fixation (CF) which are two laboratory tests that can be used to detect infection with human herpesvirus by testing for the presence of antibodies against the virus or antigens of the virus.

Serological methods can also be useful when one wishes to detect antibody to a specific viral variant. For example, one may wish to see how well a vaccine recipient has responded to a new preparation by assay of patient sera.

IIA. Vector, Cell Line and Transgenic Mammal

This invention provides a replicable vector containing the isolated nucleic acid molecule encoding VP26. The vector includes, but is not limited to: a plasmid, cosmid, λ phage or yeast artificial chromosome (YAC) which contains the isolated nucleic acid molecule.

To obtain the vector, for example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are available and well-known to those skilled in the art.

This invention provides a host cell containing the vector. Suitable host cells include, but are not limited to, bacteria (such as *E. coli*), yeast, fungi, plant, insect and mammalian cells. Suitable animal cells include, but are not limited to Vero cells, HeLa cells, Cos cells, CV1 cells and various primary mammalian cells.

This invention provides a transgenic nonhuman mammal which comprises the isolated nucleic acid molecule introduced into the mammal at an embryonic stage. Methods of producing a transgenic nonhuman mammal are known to those skilled in the art.

III. Diagnostic Assays for KS

This invention embraces diagnostic kits for detecting the presence of a KS agent in biological samples, such as skin samples or samples of other affected tissue, comprising a container containing a nucleic acid sequence specific for KSHV VP26 and instructional material for detecting the KS-associated herpesvirus. A container containing nucleic acid primers to any one of such sequences is optionally included.

This invention further embraces diagnostic kits for detecting the presence of a KS agent in biological samples, such as serum or solid tissue samples, comprising a container containing antibodies to KSHV VP26, and instructional material for performing the test. Alternatively, inactivated viral particles or polypeptides derived from the human herpesvirus may be used in a diagnostic kit to detect antibodies specific for KSHV VP26.

A. Nucleic Acid Assays

This invention provides a method of diagnosing Kaposi's sarcoma in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated nucleic acid, under hybridizing conditions; and. (c) determining the presence of the nucleic acid molecule hybridized, the presence of which is indicative of Kaposi's sarcoma in the subject, thereby diagnosing Kaposi's sarcoma in the subject.

In one embodiment the nucleic acid molecule from the tumor lesion is amplified before step (b). In another embodiment PCR is employed to amplify the nucleic acid molecule. Methods of amplifying nucleic acid molecules are known to those skilled in the art.

A person of ordinary skill ir. the art will be able to obtain appropriate nucleic acid sample for diagnosing Kaposi's sarcoma in the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the Nucleic acid fragments into a solid matrix may be employed before a hybridization step. One example of such solid matrix is nitrocellulose paper.

This invention provides a method of diagnosing Kaposi's sarcoma in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated Nucleic acid, under hybridizing conditions; and (c) determining the presence of the nucleic acid molecule hybridized, the presence of which is indicative of Kaposi's sarcoma in the subject, thereby diagnosing Kaposi's sarcoma in the subject.

This invention provides a method of detecting expression of a DNA virus associated with Kaposi's sarcoma in a cell which comprises obtaining total cDNA obtained from the cell, contacting the cDNA so obtained with a labelled nucleic acid molecule under hybridizing conditions, determining the presence of cDNA hybridized to the molecule, and thereby detecting the expression of the DNA virus. In one embodiment mRNA is obtained from the cell to detect expression of the DNA virus.

Accepted means for conducting hybridization assays are known and general overviews of the technology can be had from a review of: *NucleIc Acid Hybridization: A Practical Approach* (1985) Ed. Hames, B. D. and Higgins, S. J., IRL Press; *Hybridization of Nucleic Acids Immobilized on Solid Supports*, Meinkoth, J. and Wahl, G.; *Analytical Biochemistry* (1984) 238:267–284 and Innis et al., *PCR Protocols* (1990) Academic Press, San Diego.

Target-specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of KSHV, nucleic acid probes are about 50 to 1000 nucleotides, most preferably about 200 to 400 nucleotides.

A specific nucleic acid probe can be RNA or DNA or oligonucleotide, or their analogs. The probes may be single or double stranded nucleic acid molecules. The probes of the invention may be synthesized enzymatically, using methods well known in the art (e.g., nick translation, primer extension, reverse transcription, the polymerase chain reaction, and others) or chemically (e.g., by methods described by Beaucage and Carruthers or Matteucci, et al., supra).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

For discussions of nucleic acid probe design and annealing conditions see, for example, Ausubel, F., et al., supra; Berger, S. and Kimmel, A. Eds., Methods in Enzymology Vol. 152, (1987) Academic Press, New York; or *Hybridization with Nucleic Acid Probes*, pp. 495–524, (1993) Elsevier, Amsterdam.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

The following stringent hybridization and washing conditions will be adequate to distinguish a specific probe (e.g., a fluorescently labeled nucleic acid probe) from a probe that is riot specific: incubation of the probe with the sample for 12 hours at 37° C. in a solution containing denatured probe, 50% formamide, 2× SSC, and 0.1% (w/v) dextran sulfate, followed by washing in 1× SSC at 70° C. for 5 minutes; 2× SSC at 37° C. for 5 minutes; 0.2× SSC at room temperature for 5 minutes, and H$_2$O at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions. To evaluate specificity, probes can be tested on host cells containing KSHV and compared with the results from cells containing non-KS-associated virus.

It will be apparent to those of ordinary skill in the art that a convenient method for determining whether a probe is specific for a KS-associated viral nucleic acid utilizes a Southern blot (or Dot blot) using DNA prepared from one or more KS-associated human herpesviruses of the invention. Briefly, to identify a target-specific probe, DNA is isolated from the virus. Test DNA, either viral or cellular, is transferred to a solid (e.g., charged nylon) matrix. The probes are labelled by conventional methods. Following denaturation and/or prehybridization steps known in the art, the probe is hybridized to the immobilized DNAs under stringent conditions, such as defined above.

It is further appreciated that in determining probe specificity and in utilizing the method of this invention to detect KS-associated herpesvirus, a certain amount of background signal is typical and can easily be distinguished by one of skill from a specific signal. Two fold signal over background is acceptable.

A preferred method for detecting the KS-associated herpesvirus is the use of PCR and/or dot blot hybridization. The presence or absence of an KS agent for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer may be used for the detection of message in samples of RNA or reverse transcriptase PCR and cDNA can be detected by methods described above. This procedure is also well known in the art. See Sambrook, et al. (1989) *Molecular Cloning: A Laboratory Manual* (2nd ed.), Cold Spring Harbor Laboratory, Vols. 1–3.

An alternative means for determining the presence of the human herpesvirus is in situ hybridization, or more recently, in situ polymerase chain reaction. In situ PCR is described in Neuvo et al. (1993) Intracellular localization of PCR-amplified hepatitis C DNA, in *American Journal of Surgical Pathology* 17(7), 683–690; Bagasra et al. (1992) Detection of HIV-1 provirus in mononuclear cells by in situ PCR, in *J. New England Journal of Medicine* 326(21):1385–1391; and Heniford et al. (1993) Variation in cellular EGF receptor mRNA expression demonstrated by in situ reverse transcriptase polymerase chain reaction, in *Nucleic Acids Research* 21(14) :3159–3166. In situ hybridization assays are well known and are generally described in *Methods Enzymol*. Vol. 152, (1987) Berger, S. and Kimmel, A. ed., Academic Press, New York. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above-described probes are also useful for in-situ hybridization or in order to locate tissues which express the gene, or for other hybridization assays for the presence of the gene or its mRNA in various biological tissues. In-situ hybridization is a sensitive localization method which is not dependent on expression of polypeptide antigens or native vs. denatured conditions.

Synthetic oligonucleotide (oligo) probes and riboprobes made from KSHV phagemids or plasmids are also provided. Successful hybridization conditions in tissue sections is readily transferrable from one probe to another. Commercially-synthesized oligonucleotide probes are prepared using the nucleotide sequence of the identified gene. These probes are chosen for length (45–65 mers), high G–C content (50–70%) and are screened for uniqueness against other viral sequences in GenBank.

Oligos are 3' end-labeled with [α-$^{35}$S]dATP to specific activities in the range of $1\times10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 μm intervals and thawed onto 3-aminopropyltriethoxysilane treated slides and allowed to air dry. The slides are then fixed in 4% freshly prepared paraformaldehyde and rinsed in water. Formalin-fixed, paraffin embedded KS tissues cut at 6 μm and baked onto glass slides can also be used. These sections are then deparaffinized in xylenes and rehydrated through graded alcohols. Prehybridization in 20 mM Tris Ph 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (Ph 7.4), 3× SSC, 1× Denhardt's solution, 100 ug/ml salmon sperm DNA, 125 ug/ml yeast tRNA and the oligo probe ($10^6$ cpm/ml) at 42° C. overnight. The slides are washed twice with 2× SSC and twice with 1× SSC for 15 minutes each at room temperature and visualized by autoradiography. Briefly, sections are dehydrated through graded alcohols containing 0.3M ammonium acetate and air dried. The slides are dipped in Kodak NTB2 emulsion, exposed for days to weeks, developed, and counterstained with hematoxylin and eoxin. Alternative immunohistochemical protocols may be employed which are known to those skilled in the art.

B. Immunologic Assays

This invention provides a method of diagnosing a DNA virus in a subject, which comprises (a) obtaining a suitable bodily fluid sample from the subject, (b) contacting the suitable bodily fluid of the subject to a support having already bound thereto a Kaposi's sarcoma antibody, so as to bind the Kaposi's sarcoma antibody to a specific Kaposi's sarcoma antigen, (c) removing unbound bodily fluid from the support, and (d) determining the level of Kaposi's sarcoma antibody bound by the Kaposi's sarcoma antigen, thereby diagnosing the subject for Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto a Kaposi's sarcoma antigen, so as to bind Kaposi's sarcoma antigen to a specific Kaposi's sarcoma antibody, (c) removing unbound bodily fluid from the support, and (d) determining the level of the Kaposi's sarcoma antigen bound by the Kaposi's sarcoma antibody, thereby diagnosing Kaposi's sarcoma.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other assay methods are known to those skilled in the art. Also known to those skilled in the art are methods to avoid cross-reactivity with other antigens, e.g., antigens from EBV or other viruses, by selecting the most dissimilar polypeptide sequence of VP26 from KSHV in order to maximize assay specificity for KSHV. Further, a subject infected with KSHV may be diagnosed with the above-described methods.

The detection of the human herpesvirus and the detection of virus-associated KS are essentially identical processes. The basic principle is to detect the virus using specific ligands that bind to the virus but not to other polypeptides or nucleic acids in a normal human cell or its environs. The ligands can either be nucleic acid or antibodies. The ligands can be naturally occurring or genetically or physically modified, such as Fab or chimeric antibodies. Serological tests for detection of antibodies to the virus may also be performed by using polypeptide antigens obtained from the human herpesvirus, as described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS is present.

See Immunoassays above for more details on the immunoreagents of the invention for use in diagnostic assays for KS.

IV. Treatment of Human Herpesvirus-Induced KS

This invention provides a method for treating a subject with Kaposi's sarcoma (KS) comprising administering to the subject having KS a pharmaceutically effective amount of an antiviral agent in a pharmaceutically acceptable carrier, wherein the agent is effective to treat the subject with KS-associated human herpes virus.

Further, this invention provides a method of prophylaxis or treatment for Kaposi's sarcoma (KS) by administering to a patient at risk for KS, an antibody that binds to the human herpesvirus in a pharmaceutically acceptable carrier. In one embodiment the antiviral drug is used to treat a subject with the DNA herpesvirus of the subject invention.

This invention provides a method of treating a subject with Kaposi's sarcoma, comprising administering to the subject an effective amount of an antisense molecule capable of hybridizing to the isolated DNA molecule under conditions such that the antisense molecule selectively enters a tumor cell of the subject, so as to treat the subject.

A. Nucleic Acid Therapeutics

This invention provides an antisense molecule capable of hybridizing to the isolated nucleic acid molecule. In one embodiment the antisense molecule is DNA. In another embodiment the antisense molecule is RNA. In another embodiment, the antisense molecule is a nucleic acid derivative (e.g., DNA or RNA with a protein backbone).

The present invention extends to the preparation of antisense nucleic acids and ribozymes that may be used to interfere with the expression of proteins either by masking the mRNA with an antisense nucleic acid or cleaving it with a ribozyme, respectively.

This invention provides inhibitory nucleic acid therapeutics which can inhibit the activity of herpesviruses in patients with KS. Inhibitory nucleic acids may be single-stranded nucleic acids, which can specifically bind to a complementary nucleic acid sequence. By binding to the appropriate target sequence, an RNA—RNA, a DNA—DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene, C. and Toulme, J. (1990) *Biochim. Biophys. Acta.* 1049:99–125, which is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. (1988) *PNAS* 85:1028–1032 and Harel-Bellan, A., et al. (1988) *Exp. Med.* 168:2309–2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation, as described in Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

An example of an antiherpes virus inhibitory nucleic acid is ISIS 2922 (ISIS Pharmaceuticals) which has activity against CMV (see *Biotechnology News* 14:5).

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

B. Antiviral Agents

The use of combinations of antiviral drugs and sequential treatments are useful for treatment of herpesvirus infections and will also be useful for the treatment of herpesvirus-induced KS. For example, Snoeck et al. (1992) *Eur. J. Clin. Micro. Infect. Dis.* 11:1144–55, found additive or synergistic effects against CMV when combining antiherpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. (1991) *Antimicrob Agents Chemother* 35:2440–3.

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. (1990) *Mol. Pharm.* 37,402–7) describes the use of thymilydate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophalactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach, S. L., et al. (1992) *Infec-* tious Disease Ch.35:2839, W. B. Saunders, Philadelphia, Pa.) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

The antiherpesvirus agents that will be useful for treating virus-induced KS can be grouped into broad classes based on their presumed modes of action. These classes include agents that act (1) by inhibition of viral DNA polymerase, (2) by targeting other viral enzymes and proteins, (3) by miscellaneous or incompletely understood mechanisms, or (4) by binding a target nucleic acid (i.e., inhibitory nucleic acid therapeutics, supra). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of DNA polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al., supra).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al. (1990) *Antiviral Research* 14:61–74) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq (1993; *Antimicrobial Chemotherapy* 32, Suppl. A, 121–132) and in other references cited supra and infra.

Anti-herpesvirus medications suitable for treating viral induced KS include, but are not limited to, nucleoside analogs including acyclic nucleoside phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosyl-cytosine (ara-C); HPMPC [(S)-1-[3-hydroxy-2-(phosphonylmethoxy)propyl]cytosine (e.g., GS 504, Gilead Science)] and its cyclic form (cHPMPC) HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP[9-(2-phosphonyl-methoxyethyl)-2,6-diaminopurine]; HOE 602 [2-amino-9-(1,3-bis(isopropoxy)-2-propoxymethyl)purine]; PMEA [9-(2-phosphonylmethoxyethyl)adenine]; bromovinyl-deoxyuridine (Burns and Sandford, 1990, *J. Infect. Dis.* 162:634–7); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al., supra); and 5-mercutithio analogs of 2'-deoxyuridine (Holliday, J., and Williams, M. V., 1992, *Antimicrob. Agents Chemother.* 36:1935); acyclovir [9-([2-hydroxyethoxy]methyl)guanine; e.g., Zovirax (Burroughs Wellcome)]; penciclovir (9-[4-hydroxy-2-(hydroxymethyl) butyl]-guanine); ganciclovir [(9-[1,3-dihydroxy-2 propoxymethyl]-guanine) e.g., Cymevene, Cytovene (Syntex), DHPG (Stals et al., 1993, *Antimicrobial Agents Chemother.* 37: 218–23; isopropylether derivatives of ganciclovir (see, e.g., Winkelmann et al., 1988, *Drug Res.* 38, 1545–48); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(+−)-9-[1β,2α,3β)-2,3-bis (hydroxymethyl)-1-cyclobutyl]adenine], cyclobut-G [(+−)-9-[1β,2α,3β)-2,3-bis(hydroxymethyl)-1-cyclobutyl] guanine], BHCG [(R)-(1α,2β,1α)-9-(2,3-bis (hydroxymethyl)cyclobutyl]guanine], and an active isomer of racemic BHCG, SQ 34,514 [1R-1α,2β,3α)-2-amino-9-[2,3-bis(hydroxymethyl)cyclobutyl]-6H-purin-6-one (see, Braitman et al., 1991, *Antimicrob. Agents and Chemotherapy* 35:1464–8). Certain of these antiherpesviral agents are discussed in Gorach et al., 1992, *Infectious Disease* Ch.35:289, W. B. Saunders, Philadelphia; Saunders et al., 1990, *J. Acquir. Immune Defic. Syndr.* 3:571; Yamanaka et al., 1991, *Mol. Pharmacol.* 40:446; Greenspan et al., 1990, *J. Acquir. Immune Defic. Syndr.* 3:571.

Triciribine and triciribine monophosphate are potent inhibitors against herpes viruses. (Ickes et al., 1994, *Antiviral Research* 23, seventh International Conf. on Antiviral Research, Abstract No. 122, Supp. 1.), HIV-1 and HIV-2 (Kucera et al., 1993, *AIDS Res. Human Retroviruses* 9:307–314) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella- Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble, 1991, *Clinical Infectious Diseases* 14:741–6. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK- HSV, VZV or CMV infections in animal models (De Clercq, supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythrooxetanosyl)guanine]. Although OXT-G is believed to act by inhibiting viral DNA synthesis its mechanism of action has not yet been elucidated. These and other compounds are described in Andrei et al., 1992, *Eur. J. Clin. Microbiol. Infect. Dis.* 11:143–51. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Other Antivirals

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target. of, e.g., 1-[2-(hydroxymethyl) cycloalkylmethyl]-5-substituted -uracils and -guanines as described in, e.g., U.S. Pat. Nos. 4,863,927 and 4,782,062 (Tolman et al., Merck) as well as other enzymes. It will be apparent to one of ordinary skill in the art that there are additional viral proteins, both characterized and as yet to be discovered, that can serve as target for antiviral agents.

Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I)·Poly($C_{12}U$), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) (see, *The Pink Sheet* 55(20) May 17, 1993).

Interferon is known inhibit replication of herpes viruses. See Oren and Soble, supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and U.S. Pat. No. 5,175,165 (Blumenkopf et al.; Burroughs Wellcome). U.S. Pat. No. 4,880,820 (Ashton et al., Merck) describes the antiherpes virus agent (S)-9-(2,3-dihydroxy-1-propoxymethyl)guanine.

U.S. Pat. No. 4,708,935 (Suhadolnik et al., Research Corporation) describes a 3'-deoxyadenosine compound effective in inhibiting HSV and EBV. U.S. Pat. No. 4,386,076 (Machida et al., Yamasa Shoyu Kabushiki Kaisha) describes use of (E)-5-(2-halogenovinyl)-arabincfuranosyluracil as an antiherpesvirus agent. U.S. Pat. No. 4,340,599 (Lieb et al., Bayer Aktiengesellschaft) describes phosphonohydroxyacetic acid derivatives useful as antiherpes agents. U.S. Pat. Nos. 4,093,715 and 4,093,716 (Lin et al., Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al., Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein EBarr virus.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA. virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy

Having identified a primary causal agent of KS in humans as a novel human herpesvirus, there are immunosuppressive therapies that can modulate the immunologic dysfunction that arises from the presence of viral-infected tissue. In particular, agents that block the immunological attack of the viral-infected cells will ameliorate the symptoms of KS and/or reduce disease progression. Such therapies include antibodies that prevent immune system targeting of viral-infected cells. Such agents include antibodies which bind to cytokines that otherwise upregulate the immune system in response to to viral infection.

The antibody may be administered to a patient either singly or in a cocktail containing two or more antibodies, other therapeutic agents, compositions, or the like, including, but not limited to, immuno-suppressive agents, potentiators and side-effect relieving agents. Of particular interest are immuno-suppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides substances suitable for use as vaccines for the prevention of KS and methods for administering them. The vaccines are directed against KSHV and most preferably comprise antigens obtained from KSHV. In one embodiment, the vaccine contains attenuated KSHV. In another embodiment, the vaccine contains killed KSHV. In another embodiment, the vaccine contains a nucleic acid vector encoding KSHV VP26. In another embodiment, the vaccine is a subunit vaccine containing KSHV VP26. In another embodiment, the vaccine contains KSHV VP26.

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administered to the subject in an effective amount to vaccinate the subject against Kaposi's sarcoma.

This invention provides a method of immunizing a subject against disease caused by KSHV which comprises administering to the subject an effective immunizing dose of an isolated herpesvirus subunit vaccine.

A. Vaccines

The vaccine can be made using synthetic peptide or recombinantly-produced polypeptide described above as antigen. Typically, a vaccine will include from about 1 to 50 micrograms of antigen. More preferably, the amount of polypeptide is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049. More conventionally, an antigen can be conjugated to a suitabLe carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," Bioconjugate Chem. 1:2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al., 1990, Inf. Dis. Clin. N. Amer. 4:159; Hardy, I. et al., 1991, New Enql. J. Med. 325:1545; Levin, M. J. et al., 1992, J. Inf. Dis. 166:253; Gershon, A. A., 1992, J. Inf. Des. 166(Suppl):563. Vaccines against Herpes simplex Types 1 and 2 are also commercially available with some success in protection against primary disease, but have been less successful in preventing the establishment of latent infection in sensory ganglia (Roizman, B., 1991, Rev. Inf. Disease 13(Suppl. 11):S892; Skinner, G. R. et al., 1992, Med. Microbiol. Immunol. 180:305).

Vaccines against KSHV can be made from the KSHV envelope glycoproteins. These proteins can be purified and used for vaccination (Lasky, L. A., 1990, *J. Med. Virol.* 31:59). MHC-binding peptides from cells infected with the human herpesvirus can be identified for vaccine candidates per the methodology of Marloes, et al., 1991, *Eur. J. Immunol.* 21:2963–2970.

The KSHV antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 μg to about 100 μg protein per patient. A preferable range is from about 1 μg to about 50 μg per dose. A more preferred range is about 15 μg to about 45 μg. A suitable dose size is about 0.5 ml. Accordingly, a dose for intramuscular injection, for example, would comprise 0.5 ml containing 45 μg of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intra-muscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral polypeptides from the human herpesvirus. For example, it is known in the protein art that certain amino acid residues can be substituted with amino acids of similar size and polarity without an undue effect upon the biological activity of the protein. The human herpesvirus proteins have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic. bases such as, for example, sodium, potassium, ammonium, calcium, or ferric hydroxides, and such organic bases as isopropylamine, trimethylamine, 2-ethylamino ethanol, histidine, procaine, and the like.

C. Monitoring Therapeutic Efficacy

This invention provides a method for monitoring the therapeutic efficacy of treatment for Kaposi's sarcoma, which comprises determining in a first sample from a subject with Kaposi's sarcoma the presence of the isolated Nucleic acid molecule, administering to the subject a therapeutic amount of an agent such that the agent is contacted to the cell in a sample, determining after a suitable period of time the amount of the isolated nucleic acid molecule in the second sample from the treated subject, and comparing the amount of isolated nucleic acid molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays For Pharmaceuticals for Alleviating the Symptoms of KS Since an agent involved in the causation or progression of KS has been identified and described, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus polypeptides or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada, H. et al., 1989, *J. Clin. Microbiol.* 27:2204; Kikuta et al., 1989, *Lancet Oct.* 7:861). Infected cultures and their supernatants can be assayed for the total amount of virus including the presence of the viral genome by quantitative PCR, by dot blot assays, or by using immunologic methods. For example, a culture of susceptible cells could be infected with the human herpesvirus in the presence of various concentrations of drug, fixed on slides after a period of days, and examined for viral antigen by indirect immunofluorescence with monoclonal antibodies to viral polypeptides (Kikuta et al., supra). Alternatively, chemically adhered MT-4 cell monolayers can be used for an infectious agent assay using indirect immunofluorescent antibody staining to search for focus reduction (Higashi, K. et al., 1989, *J. Clin. Micro.* 27:2204).

As an alternative to whole cell in vitro assays, purified enzymes isolated from the human herpesvirus can be used as targets for rational drug design to determine the effect of the potential drug on enzyme activity, such as thymidine phosphotransferase or DNA polymerase. The genes for these two enzymes are provided herein. A measure of enzyme activity indicates effect on the agent itself.

Drug screens using herpes viral products are known and have been previously described in EP 0514830 (herpes proteases) and WO 94/04920 ($U_L13$ gene product).

This invention provides an assay for screening anti-KS chemotherapeutics. Infected cells can be incubated in the presence of a chemical agent that is a potential chemotherapeutic against KS (e.g. acyclo-guanosine). The level of virus in the cells is then determined after several days by IFA for antigens or Southern blotting for viral genome or Northern blotting for mRNA and compared to control cells. This assay can quickly screen large numbers of chemical compounds that may be useful against KS.

Further, this invention provides an assay system that is employed to identify drugs or other molecules capable of binding to the nucleic acid molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

VIII. Treatment of HIV

This invention provides a method of inhibiting HIV replication, comprising administering to the subject or treating cells of a subject with an effective amount of a polypeptide which is encoded by a nucleic acid molecule, so as to inhibit replication of HIV. In one embodiment the polypeptide is KSHV virion protein 26 (VP26).

This invention is further illustrated in the Experimental Details section which follows. This section is set forth to aid in understanding the invention but is not intended to, and should not be construed to, limit in any way the invention as set forth in the claims which follow thereafter.

EXPERIMENTAL SECTION

Representational Difference Analysis (RDA) to Identify and Characterize Unique DNA Sequences in KS Tissue.

To search for foreign DNA sequences belonging to an infectious agent in AIDS-KS, representational difference analysis (RDA) was employed to identify and characterize unique DNA sequences in KS tissue that are either absent or present in low copy number in non-diseased tissue obtained from the same patient.

This method can detect adenovirus genome added in single copy to human DNA but has not been used to identify previously uncultured infectious agents. RDA is performed by making simplified "representations" of genomes from diseased and normal tissues from the same individual through PCR amplification of short restriction fragments.

The DNA representation from the diseased tissue is then ligated to a priming sequence and hybridized to an excess of unligated, normal tissue DNA representation. Only unique sequences found in the diseased tissue have priming sequences on both DNA strands and are preferentially amplified during subsequent rounds of PCR amplification. This process can be repeated using different ligated priming sequences to enrich the sample for unique DNA sequences that are only found in the tissue of interest.

DNA (10 $\mu$g) extracted from both the KS lesion and unaffected tissue were separately digested to completion with Bam HI (20 units/$\mu$g) at 37° C. for 2 hours and 2 $\mu$g of digestion fragments were ligated to NBam12 and NBam24 priming sequences (primer sequences described in Lisitsyn et al., Science 1993). Thirty cycles of PCR amplification were performed to amplify "representations" of both genomes. After construction of the genomic representations, KS tester amplicons between 150 and 1500 bp were isolated from an agarose gel and NBam priming sequences were removed by digestion with Bam HI.

To search for unique DNA sequences not found in non-KS driver DNA, a second set of priming sequences (JBam12 and JBam24) was ligated onto only the KS tester DNA amplicons. 0.2 μg of ligated KS lesion amplicons were hybridized to 20 μg of unligated, normal tissue representational amplicons. An aliquot of the hybridization product was then subjected to 10 cycles of PCR amplification using JBam24, followed by mung bean nuclease digestion. An aliquot of the mung bean-treated difference product was then subjected to 15 more cycles of PCR with the JBam24 primer. Amplification products were redigested with Bam HI and 200 ng of the digested product was ligated to RBam12 and RBam24 primer sets for a second round of hybridization and PCR amplification. This enrichment procedure was repeated a third time using the JBam primer set.

The initial round of DNA amplification-hybridization from KS and normal tissue resulted in a diffuse banding pattern, but four bands at approximately 380, 450, 540 and 680 bp were identifiable after the second amplification-hybridization. These bands became discrete after a third round of amplification hybridization. Control RDA, performed by hybridizing DNA extracted from AIDS-KS tissue against itself, produced a single band at approximately 540 bp. The four KS-associated bands (designated KS330Bam, KS390Bam, KS480Bam, KS627Bam after digestion of the two flanking 28 bp ligated priming sequences with Bam HI) were gel purified and cloned by insertion into the pCRII vector. PCR products were cloned in the pCRII vector using the TA cloning system (Invitrogen Corporation, San Diego, Calif.).

Determination of the Specificity of AIDS-KS Unique Sequences.

To determine the specificity of these sequences for AIDS-KS, random-primed $^{32}$P-labeled inserts were hybridized to Southern blots of DNA extracted from cryopreserved tissues obtained from patients with and without AIDS. All AIDS-KS specimens were examined microscopically for morphologic confirmation of KS and immunohistochemically for Factor VIII, Ulex europaeus and CD34 antigen expression. Control tissues used for comparison to the KS lesions included 56 lymphomas from patients with and without AIDS, 19 hyperplastic lymph nodes from patients with and without AIDS, 5 vascular tumors from nonAIDS patients and 13 tissues infected with opportunistic infections that commonly occur in AIDS patients. Control DNA was also extracted from a consecutive series of 49 surgical biopsy specimens from patients without AIDS.

The tissues were collected from diagnostic biopsies and autopsies between 1983 and 1993 and stored at −70° C. Most of the 27 KS specimens were from lymph nodes dissected under surgical conditions which diminishes possible contamination with normal skin flora. All specimens were digested with Bam HI prior to hybridization.

KS390Bam and KS480Bam hybridized nonspecifically to both KS and non-KS tissues and were not further characterized. 20 of 27 (74%) AIDS-KS DNAs hybridized with variable intensity to both KS330Bam and KS627Bam, and one additional KS specimen hybridized only to KS627Bam by Southern blotting. In contrast to AIDS-KS lesions, only 6 of 39 (15%) non-KS tissues from patients with AIDS hybridized to the KS330Bam and KS6272am inserts.

Specific hybridization did not occur with lymphoma or lymph node DNA from 36 persons without AIDS or with control DNA from 49 tissue biopsy specimens obtained from a consecutive series of patients. DNA extracted from several vascular tumors, including a hemangiopericytoma, two angiosarcomas and a lymphangioma, were also negative by Southern blot hybridization. DNA extracted from tissues with opportunistic infections common to AIDS patients, including 7 acid-fast bacillus (undetermined species), 1 cytomegalovirus, 1 cat-scratch bacillus, 2 cryptococcus and 1 toxoplasmosis infected tissues, were negative by Southern blot hybridization to KS330Bam and KS627Bam.

In addition, DNA from Epstein-Barr virus-infected peripheral blood lymphocytes and pure cultures of Mycobacterium avium-complex were also negative by Southern hybridization. Overall, 20 of 27 (74%) AIDS-KS specimens hybridized to KS330Bam and 21 of 27 (78%) AIDS-KS specimens hybridized to KS627Bam, compared to only 6 of 142 (4%) non-KS human DNA control specimens ($\chi^2$= 85.02, p<$10^{-7}$ and $\chi^2$=92.4, p<$10^{-7}$ respectively).

Characterization of KS330Bam and KS627Bam

To further characterize KS330Bam (SEQ ID NO:3) and KS627Bam (SEQ ID NO:4), six clones for each insert were sequenced. The Sequenase version 2.0 (United States Biochemical, Cleveland, Ohio.) system was used and sequencing was performed according to manufacturer's instructions. Nucleotides sequences were confirmed with an Applied Biosystems 373A Sequencer in the DNA Sequencing Facilities at Columbia University.

Sequence data from KS330Bam was used to construct PCR primers to amplify a 234 bp fragment designated KS330$_{234}$. Although Southern blot hybridization detected the KS330Bam sequence in only 20 of 27 KS tissues, 25 of the 27 tissues were positive by PCR amplification for KS330$_{234}$ demonstrating that KS330Bam is present in some KS lesions at levels below the threshold for detection by Southern blot hybridization. All KS330$_{234}$ PCR products hybridized to a $^{32}$P end-labelled 25 bp internal oligomer, confirming the specificity of the PCR. Of the two AIDS-KS specimens negative for KS330$_{234}$, both specimens appeared to be negative for technical reasons: one had no microscopically detectable KS tissue in the frozen sample, and the other was negative in the control PCR amplification for the p53 gene indicating either DNA degradation or the presence of PCR inhibitors in the sample. PCR amplification of the p53 tumor suppressor gene was used as a control for DNA quality.

Except for the 6 control samples from AIDS patients that were also positive by Southern blot hybridization, none of the other 136 control specimens were positive by PCR for KS330$_{234}$. All of these specimens were amplifiable for the p53 gene, indicating that inadequate PCR amplification was not the reason for lack of detection of KS330$_{234}$ in the control tissues. Samples containing DNA from two candidate KS agents, EBV and Mycoplasma penetrans, a pathogen commonly found in the genital tract of patients with AIDS-KS were also negative for amplification of KS330$_{234}$. In addition, several KS specimens were tested using commercial PCR primers specific for mycoplasmata and primers specific for the EBNA-2, EBNA-3C and EBER regions of EBV; all were negative.

Overall, DNA from 25 (93%) of 27 AIDS-KS tissues were positive by PCR compared with DNA from 6 (4%) of 142 control tissues, including 6 (15%) of 39 non-KS lymph nodes and lymphomas from AIDS patients, 0 of 36 lymph nodes and lymphomas from nonAIDS patients and 0 of 49 consecutive biopsy specimens. Thus, $KS330_{234}$ was found in all 25 amplifiable tissues with microscopically detectable AIDS-KS, but rarely occurred in non-KS tissues, including tissues from AIDS patients.

Of the six control tissues from AIDS patients that were positive by both PCR and Southern hybridization, two patients had KS elsewhere, two did not develop KS and complete clinical histories for the remaining two patients were unobtainable. Three of the six positive non-KS tissues were lymph nodes with follicular hyperplasia taken from patients with AIDS. Given the high prevalence of KS among patients with AIDS, it is possible that undetected microscopic foci of KS were present in these lymph nodes. The other three positive tissue specimens were B cell immunoblastic lymphomas from AIDS patients. It is possible that the putative KS agent is also a cofactor for a subset of AIDS-associated lymphomas.

To determine whether KS330Bam and KS627Bam are portions of a larger genome and to determine the proximity of the two sequences to each other, samples of KS DNA were digested with Pvu II restriction enzymes. Digested genomic DNA from three AIDS-KS samples were hybridized to KS330Bam and KS627Bam by Southern blotting. These sequences hybridized to various sized fragments of the digested KS DNA indicating that both sequences are fragments of larger genomes. Differences in the KS330Bam hybridization pattern to Pvu II digests of the three AIDS-KS specimens indicate that polymorphisms may occur in the larger genome. Individual fragments from the digests failed to simultaneously hybridize with both KS330Bam and KS627Bam, demonstrating that these two Bam HI restriction fragments are not adjacent to one another.

DNA extracted from multiple uninvolved tissues from three patients with AIDS-KS were hybridized to $^{32}$p-labelled KS330Bam and KS627Bam probes as well as analyzed by PCR using the $KS330_{234}$ primers. While KS lesion DNA samples were positive for both bands, unaffected tissues were frequently negative for these sequences. KS lesions from patients A, B and C, and uninvolved skin and muscle from patient A were positive for KS330Bam and KS627Bam, but muscle and brain tissue from patient B and muscle, brain, colon, heart and hilar lymph node tissues from patient C were negative for these sequences. Uninvolved stomach lining adjacent to the KS lesion in patient C was positive by PCR, but negative by Southern blotting which suggests the presence of the sequences in this tissue at levels below the detection threshold for Southern blotting.

Sequencing of KSHV VP26

DNA from each lambda phage or cosmid was sheared by sonication and the 1–4 kilobase fraction was gel purified, blunted with Klenow and T4 DNA polymerases and subcloned into M13mp18 (linearied at HincII or SmaI). Electrocompetent XL-1 Blue cells were transformed by electroporation, supplemented with noncompetent XL 1-Blue cells, and plated. Plaques were selected which gave positive hybridization signals on plaque lifts with the original DNA clones. Subtractive hybridization was used to avoid picking plaques from those portions of the phage or cosmids that had already been sequenced in an overlapping clone. M13 phage were grown and purified using the Qiaprep 96 M13 kit and vacuum manifold (Qiagen).

Automated dideoxy cycle sequencing (Sanger et al. PNAS 74: 5463–5467, 1977) was performed using Perkin-Elmer dye primer kits (M13 −21, CS+ or FS) and run on Applied Biosystems Inc. (ABI) 373A or 377 sequenators. Enough different M13 clones were sequenced (typical read lengths of 400 bases) to provided an average 12-fold coverage of the KSHV genome.

In regions containing gaps, primer walking was done with primers custom synthesized by Perkin-Elmer (dye terminator kits FS or Ready Reaction). Similarly, dye terminator reactions were used to resolve ambiguous bases and provide additional coverage in regions spanned by less than four sequenced clones or only clones reading in one direction.

The ABI programs Factura and AutoAssembler, and the AssemblyLign (Kodak) program were used to edit and align the sequences.

Results are set forth in SEQ ID NO:1 and SEQ ID NO:5.

REFERENCES

1. Chang, Yuan, E Cesarman, M S Pessin, F Lee, J Culpepper, D M Knowles, and Patrick S Moore (1994) Identification of herpesvirus-like DNA sequences in AIDS-associated Kaposi's sarcoma. Science 265, 1865–1869.

2. Moore, Patrick S and Yuan Chang (1995) Detection of herpesvirus-like DNA sequences in Kaposi's sarcoma in patients with and those without HIV infection. New Eng J Med 332, 1181–1185.

What is claimed is:

1. An isolated nucleic acid encoding Kaposi's sarcoma-associated herpesvirus virion protein 26 having the amino acid sequence as set forth in SEQ ID NO:2.

2. The genomic DNA of claim 1.

3. The cDNA of claim 1.

4. The RNA of claim 1.

5. The DNA of claim 2 operatively linked to a promoter of RNA transcription.

6. The nucleic acid of claim 1 which is labelled with a detectable marker.

7. The nucleic acid of claim 6, wherein the marker is a radioactive label, or a colorimetric, a luminescent, or a fluorescent marker.

8. A replicable vector comprising the nucleic acid of claim 1.

9. A host cell comprising the vector of claim 8.

10. A plasmid, cosmid, λ phage or YAC comprising the nucleic acid of claim 1.

11. The eukaryotic cell of claim 9.

12. The bacterial cell of claim 9.

13. A nucleic acid of at least 14 nucleotides capable of specifically hybridizing with the nucleic acid of claim 1.

14. An antisense molecule capable of specifically hybridizing with the nucleic acid of claim 1.

* * * * *